United States Patent [19]

Murchison et al.

[11] 4,380,589

[45] Apr. 19, 1983

[54] NOVEL FISCHER-TROPSCH CATALYSTS

[75] Inventors: Craig B. Murchison, Midland, Mich.; Dewey A. Murdick, Tulsa, Okla.

[73] Assignee: The Dow Chemical Company, Midland, Mich.

[21] Appl. No.: 334,117

[22] Filed: Dec. 24, 1981

[51] Int. Cl.³ .............................................. C07C 1/04
[52] U.S. Cl. .................................... 518/714; 252/465
[58] Field of Search ......................................... 518/714

[56] References Cited

U.S. PATENT DOCUMENTS

| | | | |
|---|---|---|---|
| 2,825,700 | 3/1958 | Ashley et al. | 252/455 R X |
| 3,392,001 | 7/1968 | Lorenz et al. | 252/466 J |
| 3,507,811 | 4/1970 | Davies et al. | 252/466 J |
| 3,549,556 | 12/1970 | Dienes | 252/466 J |
| 3,625,665 | 12/1971 | Thompson | 518/704 |
| 4,151,190 | 4/1979 | Murchison et al. | 518/714 |
| 4,199,522 | 6/1980 | Murchison et al. | 518/714 |

*Primary Examiner*—Howard T. Mars
*Attorney, Agent, or Firm*—Charles J. Enright

[57] ABSTRACT

In Fischer-Tropsch reaction to form hydrocarbons from hydrogen and carbon monoxide the use of a catalyst containing:

(1) molybdenum in free or combined form;
(2) a promoter comprising an alkali or alkaline earth metal in free or combined form; and
(3) a binder comprising an iron-containing calcium aluminate cement.

13 Claims, No Drawings

NOVEL FISCHER-TROPSCH CATALYSTS

BACKGROUND OF THE INVENTION

This invention relates to Fischer-Tropsch reactions for the production of hydrocarbons and a catalyst composition used in the process.

The art is replete with examples of Fischer-Tropsch catalytic processes for making hydrocarbons from $H_2/CO$ mixtures. These processes yield olefinic, aromatic and paraffinic hydrocarbons as well as oxygenated hydrocarbons. Much of this art concerns itself with methods for improving conversion (i.e., the amount of carbon monoxide converted to the above-mentioned products), or methods for improving selectivity (i.e., the amount of carbon converted to a given desired product divided by the total carbon converted).

Many examples in the art relate to improvements in the selectivity to a desirable product such as ethylene or materials which can be thermally cracked to ethylene. Materials which can be thermally cracked to ethylene include $C_2$–$C_4$ paraffinic hydrocarbons and $C_3$–$C_4$ olefinic hydrocarbons. It is desirable to maximize the yield of ethylene in this process sub-group because losses occur when thermally cracking the other hydrocarbons to ethylene.

An example of such a process is U.S. Pat. No. 4,151,190 which discloses a method for increasing the selectivity to hydrocarbons containing 2 to 4 carbon atoms by the use of a 3-component catalyst comprising at least one material selected from the group consisting of a metal oxide or sulfide of molybdenum, tungsten, rhenium, ruthenium and platinum; at least one material selected from the group consisting of the hydroxides, oxides and salts of the alkali metals, alkaline earth metals, and thorium; and a support comprising alumina, silica, carbon, zirconia, magnesia, etc.

Another example is U.S. Pat. No. 4,199,522 which discloses a method for increasing the selectivity to $C_2$–$C_4$ olefins by using a catalyst with less than 100 $m^2/gm$ surface area and comprising at least one member of the group of metals, oxides or sulfides of molybdenum, tungsten, rhenium, ruthenium, nickel, palladium, rhodium, osmium, iridium, and platinum; and at least one member of the group of hydroxides, oxides or salts of alkali and alkaline earth metals; which catalyst may optionally be on a support comprising alumina, carbon, silica, zirconia, zircon, titanium dioxide, magnesia or mixtures thereof.

As good as these catalysts are, there is always room for improvement. It is an object of this invention to produce a Fischer-Tropsch catalyst composition which, when used in a Fischer-Tropsch process, is more selective to $C_2$–$C_4$ olefins and particularly to ethylene. It is an object of this invention to provide a process with improved yields of $C_2$–$C_4$ olefins and particularly ethylene in a Fischer-Tropsch process. While these objects are generally intended, it is not necessary for each and every possible embodiment of the invention to satisfy each of these criteria in order to be within the scope of the invention.

SUMMARY OF THE INVENTION

These objects are achieved in a process for producing hydrocarbons by contacting hydrogen and carbon monoxide in the presence of a catalyst, wherein the catalyst comprises molybdenum in free or combined form; a promoter, comprising an alkali or alkaline earth metal in free or combined form; and a binder comprising an iron-containing calcium aluminate cement.

A key feature of this invention is the unexpected interaction of the molybdenum and alkali or alkaline earth metals with an iron-containing calcium aluminate cement binder. Use of this binder improves the yield of $C_2$–$C_4$ hydrocarbons and in particular improves the yield of $C_2$–$C_4$ olefins, all of which can advantageously be used in the production of ethylene.

DETAILED DESCRIPTION OF SPECIFIC EMBODIMENTS

The hydrogen and carbon monoxide required for this process can be obtained by methods known in the art. Examples are gasification of hydrocarbonaceous materials such as coal, high specific gravity oils or natural gas; as a by-product of partial combustion cracking; or through the water-gas shift reaction. The two components may also be generated separately and combined for the subject reaction.

The molar ratio of hydrogen to carbon monoxide in the feed gas ranges generally from about 0.25 to about 4.0 and preferably from about 0.5 to about 1.5.

The hydrocarbons produced include paraffinic, olefinic and aromatic hydrocarbons as well as oxygenated hydrocarbon compounds such as alcohols, aldehydes, ketones and acids. In general, the use of the catalyst described favors production of low molecular weight paraffins and olefins. When compared with known supported catalysts, the process of the invention generally decreases the selectivity to methane.

Process conditions can vary over a broad range. Generally they will fall within the bounds known to the art. The pressure can vary from atmospheric to about 1500 psig and preferably from about 150 psig to about 500 psig. The process temperature ranges from about 150° C. to about 500° C. and preferably from about 300° C. to about 420° C.

The percentages of each catalyst component described herein are weight percent on an oxide basis. What this means is that each component is treated as if it were in an oxide form and the percent of the oxide to the total weight of oxides is reported. This simplifies analytical procedures. Iron is reported as $Fe_2O_3$. The components may not necessarily be and often are not present as the oxides. For example, iron and titanium may actually be present as $FeTiO_3$ (ilmenite).

The molybdenum may be present in "free or combined form" which means that it may be present as a metal, an alloy or a compound of the element. Representative compounds include molybdenum sulfides, carbides, oxides, halides, nitrides, borides, silicilides, oxyhalides, carboxylates such as acetates, acetylacetonates, oxalates, etc., hexacarbonyls, and the like. Representative compounds also include the molybdates such as alkali, alkaline earth, rare earth, and actinide series molybdates or phosphomolybdates. The free metal oxides and carbides are preferred. $MoO_3$ is a most preferred molybdenum source. The presence of other active catalytic materials is within the scope of the invention, however, preferably this component of the catalyst consists essentially of molybdenum in free or combined form.

The promoter may consist essentially of an alkali metal or alkaline earth metal, in free or combined form. Alkali metals include: lithium, sodium, potassium, rubidium and cesium. Alkaline earth metals include: beryllium, magnesium, calcium, strontium and barium. Alkali metals and particularly sodium and potassium are preferred. Potassium is most preferred. The promoter may be present in free or combined form as a metal, oxide or hydroxide, or as a salt or a combination of these. The promoter is generally present in an amount of at least about 0.05 weight percent on an oxide basis of the finished catalyst. Preferably, it is present in an amount of at least about 0.1 percent and most preferably at least 0.5 percent. Large amounts up to 50 percent of the promoter may be present. Preferably the promoter is present at less than 10 percent and most preferably less than 2 percent. The promoter may be added as an ingredient to the mix to make the catalyst or may be a part of one of the other components such as potassium molybdate or alkali in the cement.

The binder used is a cementitious material. The binder may consist essentially of an iron-containing calcium aluminate cement. Calcium aluminate cements or high alumina cements are described in the cement article in Kirk-Othmer's *Encyclopedia of Chemical Technology*, 3rd Ed., Vol. V, page 187, and which article is incorporated herein by reference. Titanium may be inherently present in the cement or may be added to the binder, for example, as a titania powder.

The binder also contains iron. This iron may be added to the binder as iron oxide powder, as a soluble iron salt, as an iron compound with another component of the cement or as an inherent portion of the dry cement. The binder contains iron, generally at a level of at least 0.1 percent, preferably at a level of at least about 2.0 percent on an oxide basis. Most perferably the iron is present at at least about 5.0 percent on an oxide basis. Preferably the iron will be present at less than 15.0 percent of the binder on an oxide basis. The cement used in the binder is a calcium aluminate cement. A suitable cement is available from Universal Atlas Cement Division of United States Steel and is designated Atlas Lumnite ® calcium aluminate cement. A nominal analysis of this cement as supplied by the manufacturer is:

TABLE I

| $Al_2O_3 + TiO_2$ | 44.0 percent |
|---|---|
| $Fe_2O_3$ | 8.5 percent |
| CaO | 35.8 percent |
| $SiO_2$ | 8.6 percent |
| MgO | 0.7 percent |
| $SO_3$ | 1.7 percent |

The calcium aluminate cement may also contain other incidental materials which do not adversely affect the reaction. Typically, commercially available calcium aluminate cements contain titania, iron oxides, silica, magnesia and sulfur, generally as a sulfate.

The generally acceptable analyses of the calcium aluminate cement binder are listed in Table II:

TABLE II

| $Al_2O_3 + TiO_2$ | 40–60 percent |
|---|---|
| $Fe_2O_3$ | 5–15 percent |
| CaO | 30–40 percent |
| $SiO_2$ | 5–15 percent |
| MgO | 0–5 percent |
| $SO_3$ | 0–3 percent |

Description of these limitations does not necessarily exclude specific embodiments of the invention which fall outside of the scope of these ranges on some particular components or which contain other nondeleterious materials.

The binder may be present as from about 1 to about 90 percent of the finished catalyst. The quantity of binder is not critical but at least about 5 percent is preferred. Greater amounts do not seem to substantially alter the product character.

The catalysts of the invention may be made by mixing dry powders of the individual components with water followed by extrusion and drying. The resulting catalyst extrudates may then be reduced in hydrogen prior to use in the Fischer-Tropsch reaction process. The water-moistened extrudates may also be held at room temperature to cure the cement and be within the scope of this invention.

The extrudates may be heated in air, hydrogen, nitrogen or other atmosphere to obtain the metallic elements in their final catalytic form. Calcination in air at a temperature of about 250° C. to about 500° C. followed by reduction with hydrogen between 400° C. and 600° C. is preferred.

For example, molybdena powder ($MoO_3$), such as Grade L or M molybdic oxide from Climax Molybdenum Co. of Greenwich, Conn., potassium carbonate and the binder are mixed with sufficient water to form a paste amenable to extrusion. The drying may be carried out at 100° C.–700° C. The molybdenum may be optionally added as some other molybdenum compound. Other means of adding the active ingredients known to those skilled in the art may also be used. For example, potassium molybdate could supply both the alkali metal promoter and the molybdenum portion of the catalyst. Other materials may be added as dry powders, for example, titania or ilmenite.

The finished catalyst can be used in a fixed bed, moving bed, fluid bed or ebullated bed processes in similar manner to known catalysts. They may be used in powdered form, as extrudates or made into other forms or shapes with or without additional binder. Catalyst surface areas are always less than 100 $m^2$/gm and are typically 5–7 $m^2$/gm.

The following examples are considered illustrative of the surprising results obtainable with the process of the invention. Elements of the catalysts are given as weight percent on an oxide basis. The percentage of each component given in the following tables is generally based on the weight of the dry powder prior to water addition and subsequent treatments of the catalyst such as calcination and reduction which tend to alter the final composition.

Subscripts, e.g., the 1 in $C_1$, etc., in all examples indicate the number of carbon atoms. Hydrocarbon analyses are reported in carbon mole percent in all examples. "Carbon mole percent" is defined as 100 times the moles of carbon present in a hydrocarbon fraction divided by the total moles of carbon in the product hydrocarbon. For example, if one mole of ethylene is found in the $C_2$ fraction, this is counted as 2 moles of carbon. The term "product hydrocarbon" excludes any carbon dioxide produced.

In the examples, an apparatus is utilized which includes in sequential order three high pressure gas bottles, a manifold, and reactors equipped on the downstream side with a fine metering valve and a rotameter, a sampling manifold and a gas chromatograph. Two bottles contain mixtures of hydrogen, carbon monoxide and nitrogen. The mixtures permit varying of the $H_2$/CO ratio from about 0.5 to about 3.0. The third bottle contains hydrogen. Each bottle is independently connected to the manifold. The manifold is constructed such that any of the three bottles may be used to feed the reactor. Through the sampling manifold the product of each reactor may be piped to the gas chromatograph for analysis.

The catalysts are loaded into ½ inch internal diameter reactors and are reduced in hydrogen before being used. The reactors are then brought to operating temperature in the presence of hydrogen. Next, feed from the high pressure gas bottle containing hydrogen and carbon monoxide is allowed to flow through the manifold to the reactor. Pressure, flow and temperature are adjusted to operating values.

The general procedure for making the catalysts of the examples is by combination of the dry powders of the ingredients and moistening with water to make a smooth but moderately stiff paste.

This paste is then extruded through an extruder such as a common laboratory syringe. The extruded paste is then dried and calcined at 100° C.–700° C. and then reduced at 400° C.–700° C. The calcining and reduction are carried out in the appropriate atmosphere to yield the desired form of the molybdenum. Calcining in air or oxygen-containing gases yields the oxide form of the catalyst. Reduction with hydrogen or other reducing gas yields the reduced forms of the molybdenum, though oxides are generally still present. Preferably, the catalysts are reduced in the reactor in which they are to be used.

EXAMPLES 1 AND 2 AND COMPARATIVE TESTS A, B AND C

The catalysts of Examples 1 and 2 and Comparative Tests A, B and C were made using the general procedure outlined above. The catalysts were extruded from a laboratory syringe and then dried and calcined in air. The extrudates were then placed in the reactors and reduced with hydrogen. In Comparative Test A the catalyst was made from 95 weight percent $MoO_3$ (Grade L or M molybdic oxide from Climax Molybdenum Co.) and 5 weight percent Lumnite ® cement. In Comparative Test B the catalyst was made from 95 weight percent Dupont LW Grade $TiO_2$ and 5 weight percent Lumnite ®. In Comparative Test C the catalyst was made with 47.5 weight percent each of $MoO_3$ and $TiO_2$ and 5 weight percent Lumnite ®. In Example 1 the catalyst was made from 87.7 weight percent $MoO_3$, 7.3 weight percent $K_2CO_3$ and 5 weight percent Lumnite ®. In Example 2 the catalyst was made from 46.3 weight percent $MoO_3$, 45.7 weight percent $TiO_2$, 3.6 weight percent $K_2CO_3$ and 5 weight percent Lumnite ®. These catalysts were compared using the procedure outlined above. Reaction conditions, yields and product analyses are given in Table III.

TABLE III

| | A | B | C | 1 | 2 |
|---|---|---|---|---|---|
| $MoO_3$ wt. % | 95.0 | — | 47.5 | 87.7 | 46.3 |
| $K_2CO_3$ wt. % | — | — | — | 7.3 | 3.6 |
| Lumnite ® wt. % | 5.0 | 5.0 | 5.0 | 5.0 | 5.0 |
| $TiO_2$ wt. % | — | 95.0 | 47.5 | — | 45.7 |
| Temperature °C. | 400 | 400 | 400 | 400 | 400 |
| Pressure (psig) | 300 | 300 | 300 | 300 | 300 |
| GHSV (hr) | 420 | 400 | 754 | 282 | 381 |
| $H_2$/CO (molar ratio) | 0.73 | 0.77 | 0.80 | 0.73 | 0.73 |
| CO Conversion | 49 | ~0 | 55 | 51 | 54 |
| Methane | 49.1 | — | 47.4 | 23.3 | 16.5 |
| Ethylene | 1.8 | — | — | 9.0 | 12.0 |
| Propylene | 1.5 | — | 1.3 | 11.3 | 15.5 |
| Butylenes | 1.0 | — | 0.2 | 4.7 | 7.5 |
| Total $C_2$—$C_4$ olefins | 4.3 | — | 1.5 | 25.0 | 35.0 |

TABLE III-continued

| | A | B | C | 1 | 2 |
|---|---|---|---|---|---|
| Ethane | 22.8 | — | 27.6 | 9.3 | 6.2 |
| Propane | 18.3 | — | 17.9 | 4.3 | 4.1 |
| Butanes | 5.5 | — | 5.3 | 1.5 | 1.7 |
| Total $C_2$—$C_4$ paraffins | 46.6 | — | 50.8 | 15.1 | 12.0 |
| % olefin in $C_2$—$C_4$ product | 8.5 | — | 2.9 | 62.0 | 74.0 |
| $C_5$ + oil | — | — | — | 36.6 | 36.5 |

The results in Table III indicate that the presence of the promoter potassium has a major effect on the catalyst and that titanium may also have a salutary effect.

COMPARATIVE TESTS D, E, F AND G

In order to demonstrate a surprising result using a catalyst made from molybdena powder and Lumnite ® binder, three prior art catalysts were tested. These are Examples 11-14 from U.S. Pat. No. 4,199,522. The results are shown in Table IV as Comparative Tests D, E, F and G, respectively.

The catalyst for Run D was $MoO_3$—30 percent; $K_2O$—5 percent; silicon-carbide support—65 percent; (Carborundum Co. product CHO analyzed as Si-C—77.9 percent, $Al_2O_3$—5.5 percent and $SiO_2$—14.9 percent with a surface area of 0.3 $m^2$/gm).

The catalyst for Run E was $MoO_3$—10 percent; $K_2O$—2 percent; MgO $Al_2O_3$ support—88 percent (surface area 30 $m^2$/gm).

The catalyst for Run F was $MoO_3$—1 percent; $K_2O$—2 percent; graphite support—97 percent (manufactured by Union Carbide Co. as BB-6 with a surface area of 1-5 $m^2$/gm).

The catalyst for Run G was $MoO_3$—30 percent; $K_2O$—4 percent; silica support—66 percent (manufactured by Johns-Manville Products as Celite 410, analyzed as $SiO_2$—86 percent, $Al_2O_3$—9 percent, CaO—1 percent, $Fe_2O_3$—2 percent, misc.—2 percent with a surface area of 3 $m^2$/gm).

TABLE IV

| | D* | E* | F* | G* |
|---|---|---|---|---|
| Temperature °C. | 420 | 407 | 420 | 366 |
| Pressure (psig) | 300 | 300 | 300 | 300 |
| GHSV (hr) | 291 | 474 | 330 | 325 |
| $H_2$/CO (molar ratio) | 0.75 | 1.1 | 0.78 | 0.78 |
| CO Conversion | 25.0 | 55.0 | 26.0 | 49.0 |
| Methane | 22.2 | 24.2 | 21.4 | 29.0 |
| Ethylene | 9.3 | 8.9 | 14.0 | 3.7 |
| Propylene | 7.3 | 12.1 | 12.3 | 11.7 |
| Butylenes | 2.9 | 6.6 | 4.6 | 6.8 |
| Total $C_2$—$C_4$ olefins | 19.5 | 27.6 | 30.9 | 22.2 |
| Ethane | 3.7 | 6.4 | 5.0 | 26.0 |
| Propane | 2.6 | 5.2 | 2.0 | 10.0 |
| Butanes | 1.1 | 0.7 | — | 4.3 |
| Total $C_2$—$C_4$ paraffins | 8.4 | 12.3 | 7.0 | 40.3 |
| % olefin in $C_2$—$C_4$ product | 69.9 | 69.2 | 81.5 | 35.5 |
| $C_5$ + oil | 50.9 | 34.5 | 40.5 | 8.5 |

*Runs D, E, F and G correspond to Example Nos. 11/A, 12/B, 13/C and 14/D, respectively, in U.S. Pat. No. 4,199,522.

EXAMPLES 3-6

In a manner similar to Example 1, the catalysts of Examples 3-6 are prepared from the components shown in Table V. The results of comparisons of Examples 3-6 in Table V show that increasing the promoter level beyond a certain point yields diminishing returns.

TABLE V

|  | 3 | 4 | 5 | 6 |
|---|---|---|---|---|
| $MoO_3$ wt. % | 46.9 | 46.6 | 46.2 | 45.6 |
| $K_2CO_3$ wt. % | 1.25 | 1.9 | 2.5 | 3.7 |
| Lumnite® wt. % | 5.0 | 5.0 | 5.0 | 5.0 |
| $TiO_2$ wt. % | 46.9 | 46.7 | 46.2 | 45.6 |
| Temperature °C. | 405 | 405 | 405 | 405 |
| Pressure (psig) | 480 | 480 | 480 | 480 |
| GHSV (hr) | 600 | 445 | 486 | 458 |
| $H_2/CO$ (molar ratio) | 0.75 | 0.75 | 0.75 | 0.75 |
| CO Conversion | 51.0 | 49.0 | 45.0 | 38.0 |
| Methane | 19.5 | 19.3 | 16.9 | 14.4 |
| Ethylene | 12.0 | 9.0 | 10.0 | 12.0 |
| Propylene | 19.9 | 18.2 | 16.8 | 16.2 |
| Butylenes | 13.1 | 9.8 | 10.2 | 11.8 |
| Total $C_2$—$C_4$ olefins | 45.0 | 37.0 | 37.0 | 40.0 |
| Ethane | 8.6 | 9.4 | 7.6 | 4.3 |
| Propane | 3.5 | 3.9 | 3.2 | 2.7 |
| Butanes | 3.7 | 2.1 | 2.3 | 3.7 |
| Total $C_2$—$C_4$ paraffins | 15.8 | 15.4 | 13.1 | 10.7 |
| % olefin in $C_2$—$C_4$ product | 74.0 | 65.0 | 74.0 | 78.0 |
| $C_5$ + oil | 19.7 | 28.3 | 33.0 | 34.9 |

EXAMPLES 7-10

In Examples 7-10 anatase and rutile forms of $TiO_2$ are compared. The catalysts are prepared in the same way as Example 1 with the components listed in Table VII. Also a lower iron calcium aluminate cement is compared. Refcon® calcium aluminate cement is commercially available from Universal Atlas and has a nominal composition as shown in Table VI.

TABLE VI

| $Al_2O_3$ + $TiO_2$ | 58.0 weight percent |
|---|---|
| $Fe_2O_3$ | 1.5 weight percent |
| CaO | 33.5 weight percent |
| $SiO_2$ | 5.6 weight percent |
| MgO | — |
| $SO_3$ | 0.4 weight percent |

The results in Table VII show that use of anatase phase of titania provides a significant improvement over the rutile form. It also shows that the higher iron content Lumnite® cement is more advantageous than the Refcon® cement.

TABLE VII

|  | 7 | 8 | 9 | 10 |
|---|---|---|---|---|
| $MoO_3$ wt. % | 46.9 | 46.9 | 46.9 | 46.9 |
| $K_2CO_3$ wt. % | 1.25 | 1.25 | 1.25 | 1.25 |
| Lumnite® wt. % | 5.0 | 5.0 | — | — |
| $TiO_2$ wt. % | 46.9 | 46.9 | 46.9 | 46.9 |
| $TiO_2$ type* | a | r | a | r |
| Refcon® cement | — | — | 5.0 | 5.0 |
| Temperature °C. | 420 | 420 | 420 | 420 |
| Pressure (psig) | 400 | 400 | 400 | 400 |
| GHSV (hr) | 794 | 756 | 391 | 684 |
| $H_2/CO$ (molar ratio) | 0.78 | 0.78 | 0.77 | 0.77 |
| CO Conversion | 62.0 | 63.0 | 47.0 | 32.0 |
| Methane | 22.6 | 27.0 | 29.0 | 29.5 |
| Ethylene | 15.0 | 10.0 | 7.0 | 8.0 |
| Propylene | 19.7 | 16.7 | 10.3 | 9.4 |
| Butylenes | 11.8 | 9.3 | 7.7 | 2.6 |
| Total $C_2$—$C_4$ olefins | 46.0 | 36.0 | 25.0 | 20.0 |
| Ethane | 8.0 | 10.7 | 10.3 | 11.7 |
| Propane | 4.7 | 5.1 | 5.4 | 3.8 |
| Butanes | 1.9 | 1.3 | 2.1 | 2.0 |
| Total $C_2$—$C_4$ paraffins | 14.6 | 17.1 | 17.8 | 17.5 |
| % olefin in $C_2$—$C_4$ product | 76.0 | 68.0 | 58.0 | 53.0 |
| $C_5$ + oil | 16.8 | 19.9 | 28.2 | 33.0 |

*a = anatase; r = rutile

EXAMPLES 11-13, COMPARATIVE TEST H

The catalysts of Examples 11-13 and Comparative Test H are made in similar fashion to Example 1 for the components listed in Table VIII. The results in Table VIII show the effect of different percentages of the calcium aluminate cement and a Portland cement. The Portland cement is not a calcium aluminate cement and does not fall within the scope of the invention. As can be seen the use of a Portland cement binder yields poorer results.

TABLE VIII

|  | 11 | 12 | 13 | H |
|---|---|---|---|---|
| $MoO_3$ wt. % | 50.0 | 50.0 | 50.0 | 50.0 |
| $K_2CO_3$ wt. % | 2.0 | 2.0 | 2.0 | 2.0 |
| Lumnite® wt. % | 10.0 | 20.0 | 40.0 | — |
| $TiO_2$ wt. % | 38.0 | 28.0 | 8.0 | 28.0 |
| Portland cement wt. % | — | — | — | 20.0 |
| Temperature °C. | 405 | 405 | 405 | 405 |
| Pressure (psig) | 470 | 470 | 470 | 470 |
| GHSV (hr) | 346 | 498 | 509 | 552 |
| $H_2/CO$ (molar ratio) | 0.77 | 0.76 | 0.78 | 0.76 |
| CO Conversion | 54.0 | 61.0 | 58.0 | 53.0 |
| Methane | 17.4 | 16.5 | 24.6 | 39.3 |
| Ethylene | 13.0 | 12.0 | 12.0 | 1.3 |
| Propylene | 14.7 | 15.9 | 16.1 | 3.1 |
| Butylenes | 8.3 | 9.1 | 10.9 | 2.6 |
| Total $C_2$—$C_4$ olefins | 36.0 | 37.0 | 39.0 | 7.0 |
| Ethane | 7.1 | 8.4 | 13.8 | 28.0 |
| Propane | 2.6 | 3.9 | 5.2 | 13.5 |
| Butanes | 1.4 | 2.0 | 2.9 | 4.3 |
| Total $C_2$—$C_4$ paraffins | 11.1 | 14.3 | 21.9 | 45.8 |
| % olefin in $C_2$—$C_4$ product | 77.0 | 72.0 | 62.0 | 13.0 |
| $C_5$ + oil | 35.5 | 32.2 | 14.5 | 7.9 |

A nominal composition for Portland cement is given in Kirk-Othmer *Encyclopedia of Chemical Technology*, 3rd Ed., Vol V, page 171 (Wiley 1979). The composition is set out in Table IX herein.

TABLE IX

| $Al_2O_3$ + $TiO_2$ | 4.5 weight percent |
|---|---|
| $Fe_2O_3$ | 3.0 weight percent |
| CaO | 63.8 weight percent |
| $SiO_2$ | 22.6 weight percent |
| MgO | 2.5 weight percent |
| $SO_3$ | 2.4 weight percent |

EXAMPLES 14-17

The catalysts of Examples 14-17 are made in a similar fashion to Example 1 from the components listed in Table X. The results in Table X set forth the effect of promoter loadings on a catalyst incorporating a Refcon® cement binder. Again a point of diminishing returns is seen.

TABLE X

|  | 14 | 15 | 16 | 17 |
|---|---|---|---|---|
| $MoO_3$ wt. % | 47.5 | 47.0 | 47.0 | 46.5 |
| $K_2CO_3$ wt. % | 0.5 | 1.0 | 1.5 | 2.0 |
| Lumnite® wt. % | — | — | — | — |
| $TiO_2$ wt. % | 47.0 | 47.0 | 46.5 | 46.5 |
| Refcon® cement wt. % | 5.0 | 5.0 | 5.0 | 5.0 |
| Temperature °C. | 400 | 400 | 400 | 400 |
| Pressure (psig) | 480 | 480 | 480 | 480 |
| GHSV (hr) | 717 | 494 | 524 | 538 |
| $H_2/CO$ (molar ratio) | 0.98 | 0.98 | 0.98 | 0.98 |
| CO Conversion | 60.0 | 54.0 | 42.0 | 39.0 |
| Methane | 44.9 | 33.2 | 29.3 | 27.1 |
| Ethylene | 0.5 | 0.5 | 8.8 | 9.0 |
| Propylene | 4.7 | 10.5 | 8.6 | 8.2 |
| Butylenes | 9.8 | 4.5 | — | — |
| Total $C_2$—$C_4$ olefins | 15.0 | 20.0 | 17.0 | 21.0 |

TABLE X-continued

|  | 14 | 15 | 16 | 17 |
|---|---|---|---|---|
| Ethane | 23.5 | 16.8 | 11.2 | 10.4 |
| Propane | 13.1 | 8.2 | 4.0 | 3.5 |
| Butanes | 3.1 | 4.1 | 2.8 | 3.3 |
| Total $C_2$—$C_4$ paraffins | 39.7 | 29.1 | 18.0 | 17.2 |
| % olefin in $C_2$—$C_4$ product | 28.0 | 41.0 | 49.0 | 55.0 |
| $C_5$ + oil | 0.4 | 17.7 | 35.3 | 34.7 |

Although the invention has been described in considerable detail, it must be understood that such detail is for the purpose of illustration only and that many variations and modifications can be made by one skilled in the art without departing from the spirit and scope of the invention.

We claim:

1. A Fischer-Tropsch process for producing hydrocarbons with improved selectivity to $C_2$-$C_4$ olefins comprising contacting hydrogen and carbon monoxide in the presence of a catalyst comprising:
   (1) molybdenum in free or combined form;
   (2) a promoter comprising an alkali or alkaline earth metal in a free or combined form; and
   (3) a binder comprising an iron-containing calcium aluminate cement.

2. The process of claim 1 wherein the catalyst further contains titanium.

3. The process of claim 2 wherein the binder contains at least about 2 percent iron on an oxide basis.

4. The process of claim 3 wherein the binder contains at least about 5 percent iron on an oxide basis.

5. The process of claim 4 wherein the binder contains on an oxide basis:

| $Al_2O_3$ + $TiO_2$ | 40–60 weight percent |
|---|---|
| $Fe_2O_3$ | 5–15 weight percent |
| CaO | 30–40 weight percent |
| $SiO_2$ | 5–15 weight percent |
| MgO | 0–5 weight percent |
| $SO_3$ | 0–3 weight percent |

6. The process of claim 1 wherein the catalyst contains from about 0.05 to about 10 percent by weight of the promoter on an oxide basis.

7. The process of claim 1 wherein the catalyst contains from about 0.1 to about 2 percent by weight of the promoter on an oxide basis.

8. The process of claim 1 wherein the catalyst contains from about one to about 90 percent of the binder.

9. The process of claim 8 wherein the catalyst contains from about one to about 20 percent of the binder.

10. The process of claim 2 wherein the titanium is present as an oxide in an anatase phase.

11. The process of claim 1 wherein the promoter comprises an alkali metal.

12. The process of claim 11 wherein the promoter comprises potassium.

13. The process of claim 1 wherein the promoter is sodium, potassium, cesium, rubidium, calcium, strontium or a mixture thereof.

* * * * *